(12) United States Patent
Sivavec et al.

(10) Patent No.: US 6,451,210 B1
(45) Date of Patent: Sep. 17, 2002

(54) METHOD AND SYSTEM TO REMOTELY MONITOR A CARBON ADSORPTION PROCESS

(75) Inventors: Timothy Mark Sivavec; Patricia Denise Mackenzie, both of Clifton Park; Joseph James Salvo, Schenectady; Sunita Singh Baghel, Rensselaer, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/716,050

(22) Filed: Nov. 20, 2000

(51) Int. Cl.$^7$ ................................................. C02F 1/28
(52) U.S. Cl. ........................... 210/662; 95/8; 95/245; 96/156; 166/53; 210/85; 210/170; 210/259; 210/263; 210/650; 210/669; 210/739; 210/747
(58) Field of Search ................... 210/85, 96.1, 143, 210/170, 259, 263, 266, 650, 662, 663, 669, 739, 747, 806; 166/53, 75.1, 267; 96/10, 214, 156; 95/8, 25, 90, 149, 243, 245

(56) References Cited

U.S. PATENT DOCUMENTS

| 4,727,936 A | | 3/1988 | Mioduszewski et al. ...... 166/53 |
|---|---|---|---|
| 4,830,757 A | * | 5/1989 | Lynch et al. ................. 210/96.1 |
| 4,839,061 A | * | 6/1989 | Manchak et al. ............ 210/170 |
| 4,844,807 A | * | 7/1989 | Manchak et al. ............ 210/170 |
| 5,069,796 A | | 12/1991 | Fox .............................. 210/747 |
| 5,122,165 A | * | 6/1992 | Wang et al. |
| 5,126,050 A | * | 6/1992 | Irvine et al. ................. 210/259 |
| 5,316,085 A | | 5/1994 | Dawson ........................ 166/53 |
| 5,399,267 A | * | 3/1995 | Wang et al. .................... 96/10 |
| 5,468,088 A | | 11/1995 | Shoemaker et al. ......... 210/747 |
| 5,639,380 A | | 6/1997 | Misquitta ..................... 210/739 |
| 5,804,743 A | | 9/1998 | Vroblesky et al. ........ 73/863.23 |
| 5,935,525 A | | 8/1999 | Lincoln et al. .............. 422/121 |
| 5,954,452 A | | 9/1999 | Goldstein .................... 405/128 |
| 5,996,423 A | | 12/1999 | Baghel et al. ............ 73/863.23 |
| 6,021,664 A | * | 2/2000 | Granato et al. .............. 210/170 |
| 6,098,448 A | | 8/2000 | Lowry et al. .................. 73/38 |

* cited by examiner

Primary Examiner—Joseph W. Drodge
(74) Attorney, Agent, or Firm—Toan P. Vo; Noreen C. Johnson (57) ABSTRACT

In a method for treating a contaminated fluid stream, a characteristic of a flow of the composition to a carbon adsorption zone is sensed. The sensing is remotely monitored to determine a treatment for the contaminated fluid stream. The contaminated fluid stream is then treated according to the monitoring. A system for treating a contaminated fluid stream comprises a sensor that senses a characteristic of a flow of a contaminated fluid stream prior to treatment and a monitor to receive information concerning the characteristic from the sensor and to consequently control the carbon adsorption zone to treat the contaminated fluid stream. The monitor is situated at a location remote from the carbon adsorption zone.

45 Claims, 5 Drawing Sheets

METHOD AND SYSTEM TO REMOTELY MONITOR A CARBON ADSORPTION PROCESS

The invention relates to a method and system for remote monitoring of a carbon adsorption process for the treatment of a contaminated fluid stream.

The Clean Air Act Amendment of 1990 (CAAA) requires efficient and economical control strategies for disposal of volatile organic compounds (VOCs). VOCs are carbon compounds that react with nitrogen oxides and other airborne chemicals in the presence of sunlight to form ozone, a primary component of smog. Under the CAAA, thousands of unregulated sources are required to reduce or eliminate VOC emissions. In addition, sources that are currently regulated will need to meet stricter regulatory requirements such as the maximum achievable control technology (MACT) requirements in Title III of the CAAA.

Carbon adsorption is a process for controlling VOC emissions. In the chemical process industry, granular activated carbon is used for water and wastewater treatment applications. An adsorption isotherm evaluation can provide useful information for designing a carbon bed unit. The evaluation can provide information on adsorpability of specific VOCs, equilibrium capacity estimates and changes in adsorption capacity relative to VOC concentration. Dynamic adsorption testing can provide other necessary design data, including required contact times and breakthrough curve. A breakthrough curve is the VOC concentration exiting the bed over time as the carbon's capacity for the VOC is reduced. In industrial and groundwater treatment applications, single-stage adsorption is commonly encountered, despite the fact that two-stage systems could permit a first carbon bed to approach saturation to obtain full carbon use.

Many times, carbon adsorption is one unit operation in an overall treatment scheme comprising several treatment modules. If the water being treated contains suspended solid, or if upstream unit operations include precipitation or settling steps for removal of metals, a separate filtration step is required. Air stripping is another unit operation that can be applied as a pretreatment to carbon adsorption for removal of VOCs. The air stripping can remove the bulk of the VOCs prior to carbon adsorption to extend bed life. Carbon adsorption can be used to treat the off-gas from the air stripper.

In some applications, VOC content of feed to a bed changes significantly over a short period. In these applications, frequent or real-time monitoring would be valuable for providing a basis for redirecting a process feed to a bed with a differing design—a design more effective or efficient for treating the changed feed. Real-time monitoring can also provide a basis for optimizing associated treatment modules to minimize VOC outputs and reduce process variation.

There is a need for a method and system to provide frequent or real-time monitoring to meet regulatory requirements and to adjust the process or associated treatment modules to improve effectiveness and efficiency of an overall carbon adsorption process.

BRIEF SUMMARY OF THE INVENTION

The present invention provides a method to monitor a carbon bed adsorption process in real time and to use the information acquired by such monitoring for optimization and control.

In a first embodiment, the invention is a method of treating a contaminated fluid stream. In the method, a characteristic of a flow of a contaminated fluid stream to a carbon adsorption zone is sensed. The sensing is remotely monitored to determine a treatment for the contaminated fluid stream. The contaminated fluid stream is then treated according to the monitoring.

In another embodiment, the invention is a system for treating a contaminated fluid stream. The system comprises a sensor that senses a characteristic of a flow of a contaminated fluid stream prior to treatment, a monitor to receive information concerning the characteristic from the sensor and to consequently control the carbon adsorption zone to treat the contaminated fluid stream. The monitor is situated at a location remote from the carbon adsorption zone.

DETAILED DESCRIPTION OF THE INVENTION

According to the invention, a method and system are provided to monitor and control the operation of carbon beds in adsorbing contaminants such as VOCs from contaminated fluid streams. Herein, the term "fluid stream" includes water environments such as industrial processing waste streams. The term particularly includes natural water environments such as aquifers, particularly groundwater and other subsurface aqueous environments. The term includes such environments in any of a gas, vapor or liquid state. Specific elements of the system include a sensing module to detect contaminants in a vapor or aqueous stream and to detect pressure build-up in a carbon bed. The sensing module can be a flow-through cell that holds a sensor and that exposes the sensor to a contaminant in the fluid stream. The sensing module can include a transceiver or set of transceivers to send a data signal from the sensor to a data collector, a data transmission system, and a remote controller.

The monitoring and control system can provide real-time monitoring to permit site operators to fine-tune carbon bed treatment operations to provide more efficient use of the beds and to optimize upstream processes to minimize VOC outputs and reduce process variation.

Figure 5:
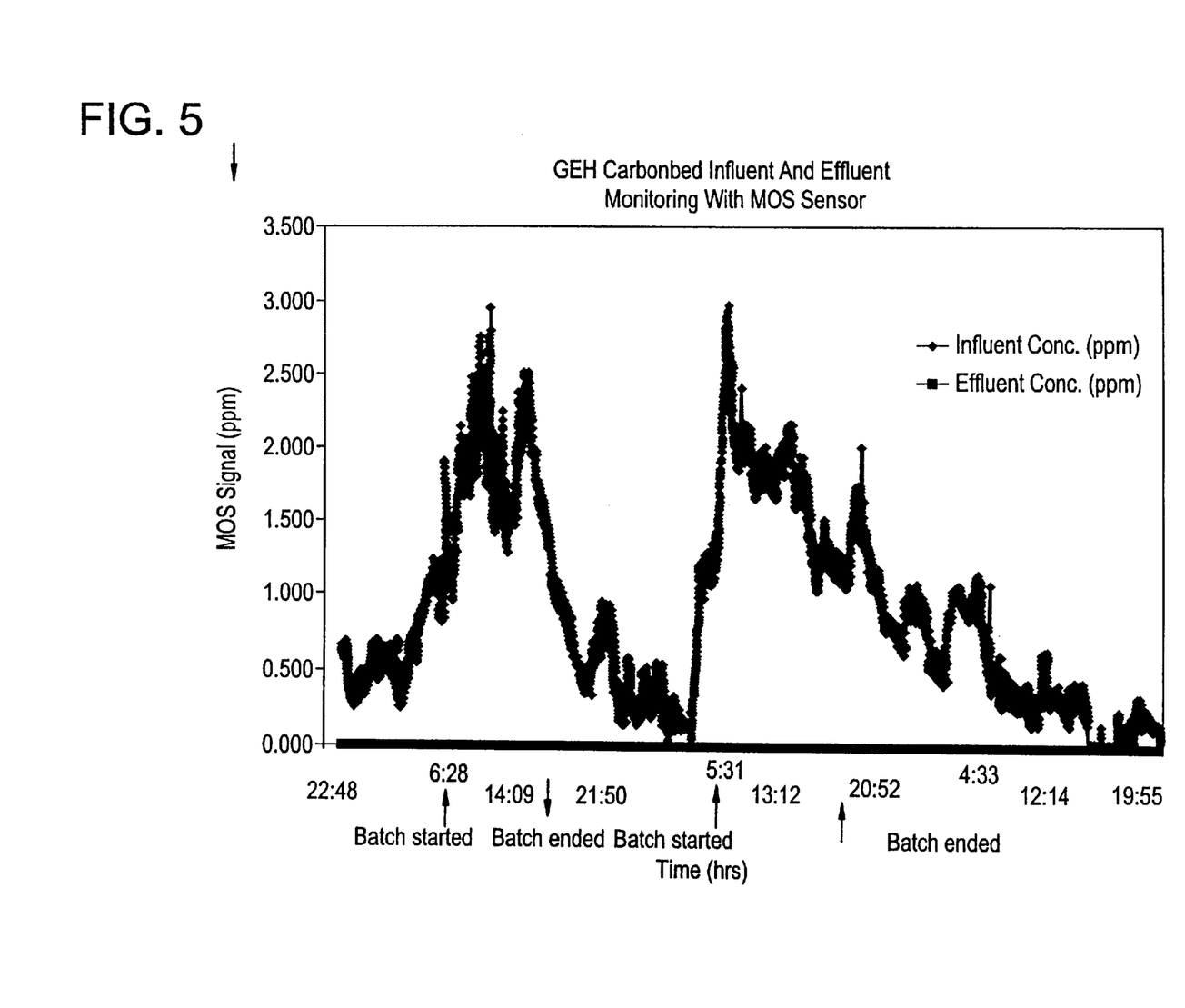
FIG. 5 is a graph of sensor signal with time.

Frequency and location of sensing modules depend upon the bed design and expected carbon bed life. Sensing modules can be situated at both an influent and an effluent line. FIG. 5 shows a graph of a carbon bed influent and effluent as monitored by MOS over time. Effluent monitoring is represented by the horizontal line at zero signal. Two batches are shown. Additionally, inter-stage sensing and monitoring can be used to provide information to determine a breakthrough curve. The resulting curve indicates when a first carbon unit has been fully used. Operations to be controlled by real-time monitoring of carbon bed pressure include backwashing, a process in which clean water is introduced through an underdrain to effect a bed expansion.

Figure 1:
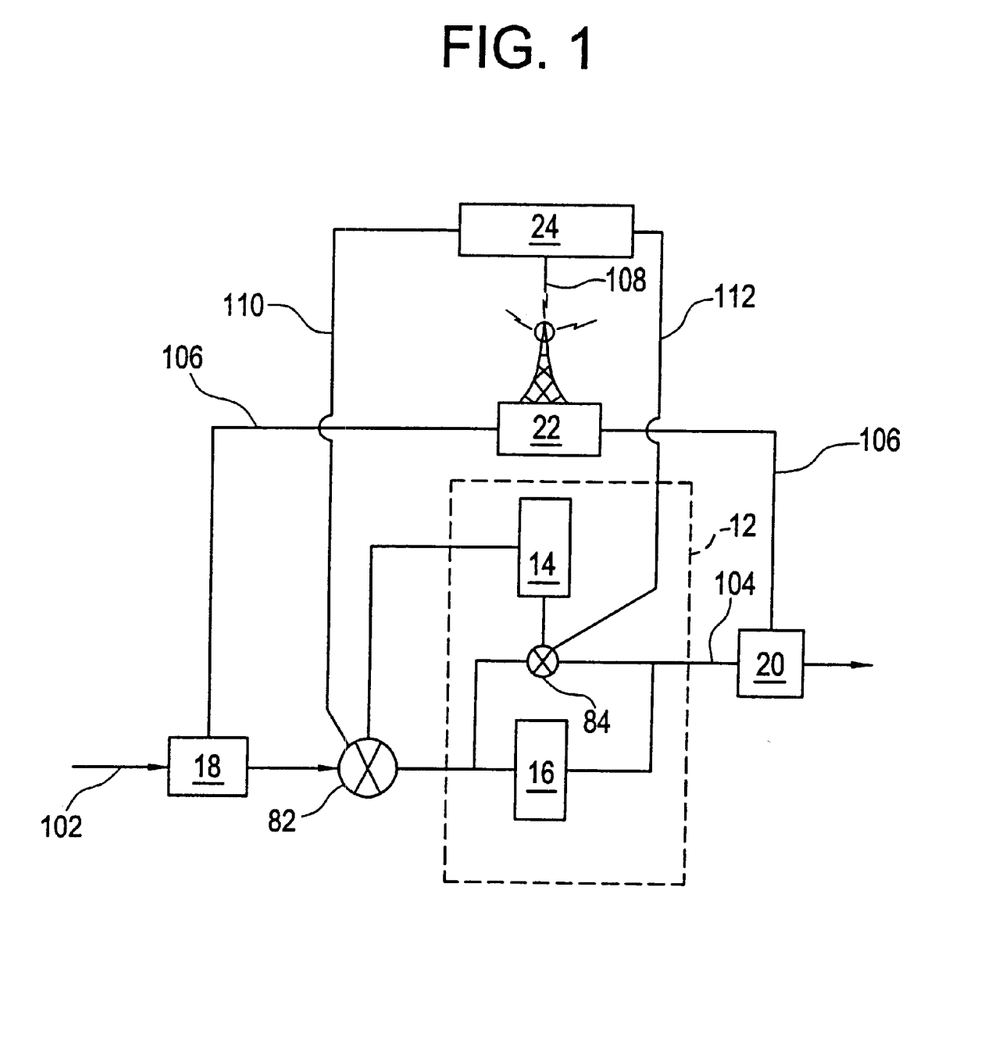
FIG. 1 is a schematic representation of a remotely monitored carbon adsorption process.
Figure 4:
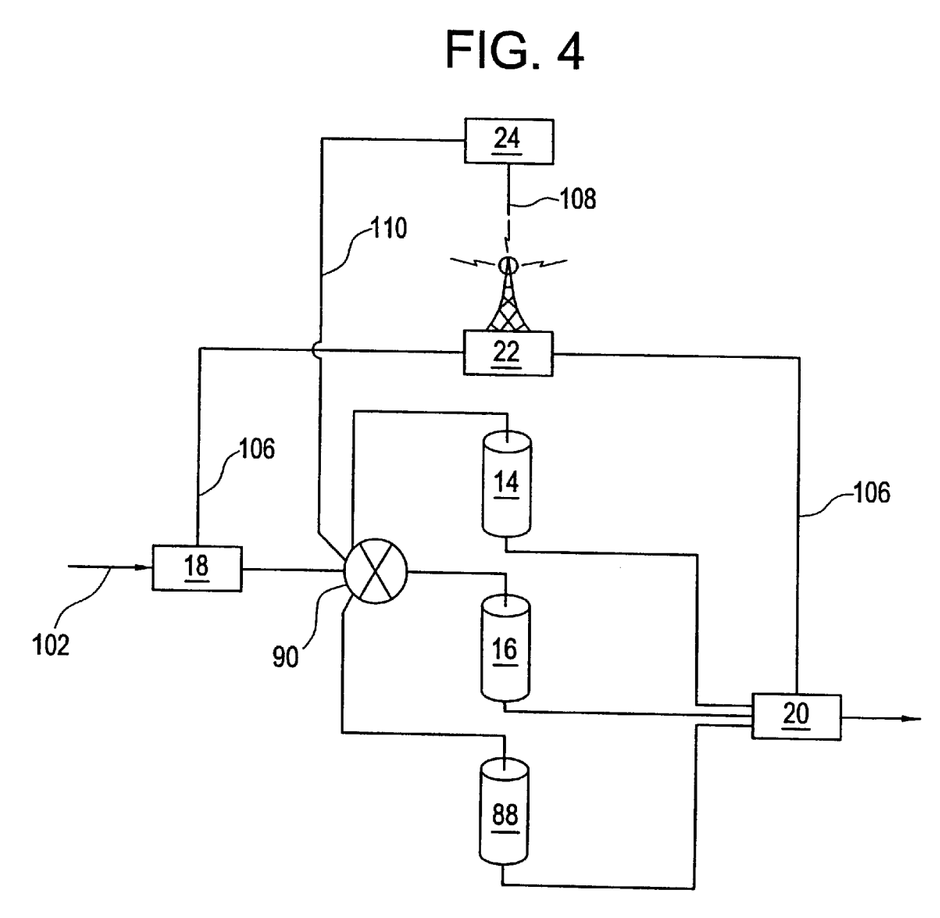
FIG. 4 is a schematic representation of another remotely monitored carbon adsorption process.

Monitoring of contaminant concentration and other parameters in the influent stream to a carbon bed can be used to determine a correct sequence of treatment. FIG. 1 shows an adsorption zone 12 with alternately connected treatment units. For example, adsorption zone 12 can include a filter or precipitation unit. A turbidity sensing unit can be used to direct an aqueous VOC stream to a filter or precipitation unit, prior to carbon bed treatment. Exam pl e s of different treatment processes or trains to which the VOC stream may be sent include ion exchange beds, air stripping columns, filters and precipitators. If VOC influent concentrations are low and meet discharge standards, treatment processing can be determined as unnecessary and the influent can be directly discharged with treated effluent or otherwise disposed. Contaminated fluid streams that contain highly adsorbable VOCs such as styrene and acrylonitrile can occasionally include difficult-to-treat butadiene. As shown in FIG. 4, when a butadiene content is sensed, an influent can be directed to a second carbon bed designed specifically to adsorb butadiene.

Real-time monitoring according to the invention enables prediction of carbon bed lifetime under site conditions. "Predictive monitoring" can provide information that can be used at other sites with similar operating conditions. Presently, accelerated column tests are used to predict column bed lifetime. However, specific testing is still required to evaluate waters with background organic compounds or special characteristics.

These and other features of the invention will become apparent from the drawings and following detailed discussion, which by way of example without limitation describe preferred embodiments.

FIG. 1 shows a parallel method and system 10 of the invention. FIG. 1 shows a carbon adsorption zone 12 comprising a plurality of carbon beds 14 and 16 connected in parallel, contaminated aqueous influent sensing module 18 connected to the feed side of the beds 14 and 16 and effluent sensing module 20 connected to the discharge side of beds 14 and 16. While the system is shown with two beds 14 and 16, the adsorption zone 12 can include any number of beds necessary for complete treatment of a contaminated fluid stream. System 10 further includes collector 22 and remotely situated controller 24.

Figure 2:
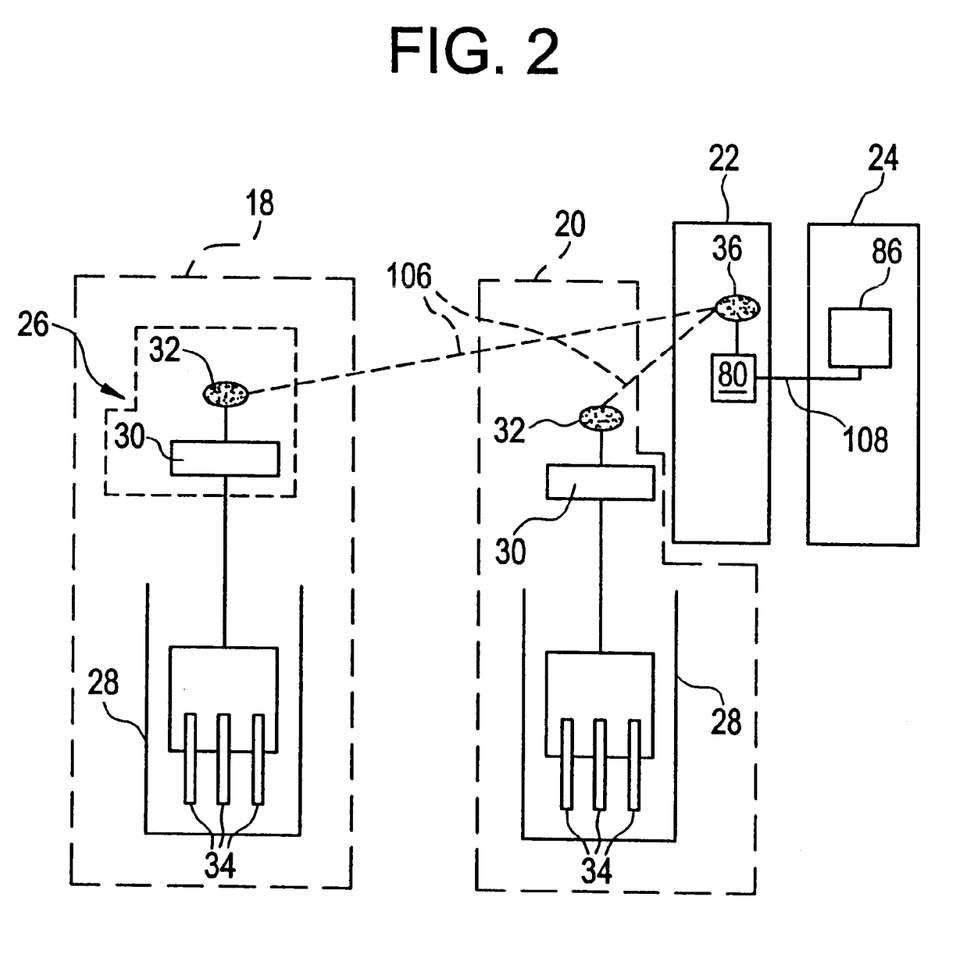
FIG. 2 is a schematic representation of a sensing and monitoring system.

A contaminated fluid stream 102 is first conveyed through influent sensing module 18 and a treated stream 104 is discharged from carbon adsorption zone 12 through effluent sensing module 20. FIG. 2 is a schematic representation of a sensing and monitoring system that includes a sensing module 18 or 20 that can be used in conjunction with a method and system according to the invention including the embodiments shown in FIG. 1 and FIG. 4. In FIG. 2, like reference numbers identify the same elements as in FIG. 1 and FIG. 4.

Referring to FIG. 2, module 18 (or 20) can generate signals (data) corresponding to one or more of the influent or effluent stream characteristics. The module 18 or 20 includes a transceiver unit 26 and an electronically coupled sensing unit 28. Transceiver unit 26 includes a receiver 30 and a transmitter 32, which is capable of transmitting data to collector 22, which can be a data collection center. The signals 106 can be communicated from transceiver unit 26 by any of a hardwired communication connection such as an electrical conductor; by a wireless communication connection such as by radio signals, by satellite communications or by combinations of wireless and hardwired connections.

Sensing unit 28 can detect a contaminant of interest or a contaminant level of interest in influent stream 102. The sensing unit 28 can include sensors 34 as shown in FIG. 2. Suitable types of sensors 34 include a chemical sensor, acoustic wave sensor, fiber optics sensor, solid-state sensor such as a metal oxide semiconductor (MOS), an electrochemical sensor and combinations of such sensors.

Figure 3:
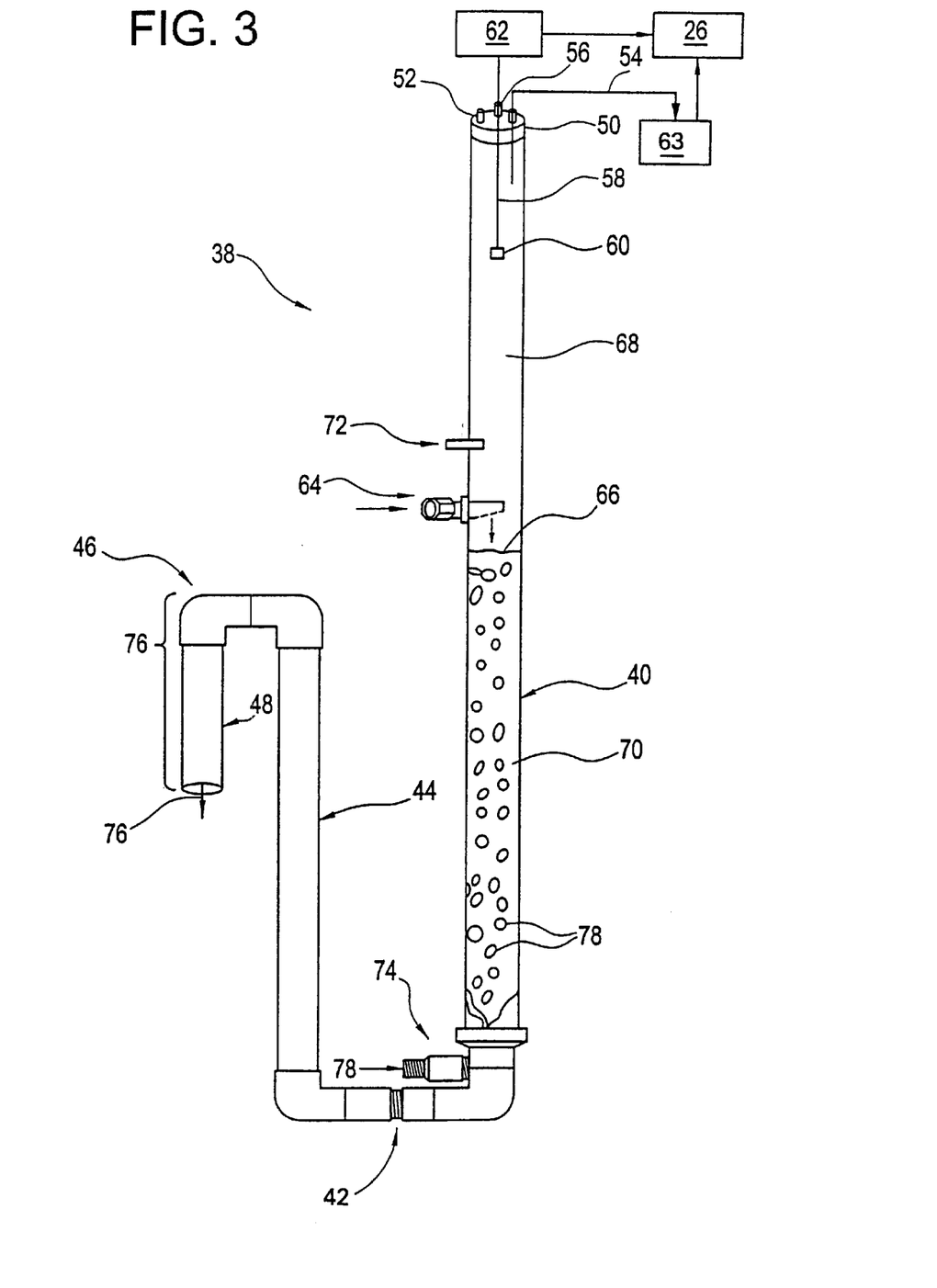
FIG. 3 is a schematic part-sectional illustration of an on-line sparging and sensing system.

A preferred sensing unit is shown in FIG. 3. FIG. 3 is an illustration of a sparger sensing unit 38, different from the unit 28 shown in FIG. 2. The unit 38 serves as an on-line sampling and sensing system that is imposed into either influent stream 102 or effluent stream 104. The on-line unit 38 comprises a sparger tubular member 40, a bottom connecting tubular member 42, a side tubular member 44, a P-trap tubular member 46 and a venting and discharge tubular member 48. The tubular members and connections in the on-line sensing unit 38 can be configured with dimensions that are sufficient to reduce or eliminate fouling and blockage by sediments or particulates.

Sparger tubular member 40 comprises a cap 50 at one end opposite connecting tubular member 42. The cap 50 comprises a plurality of ports for components. Cap exhaust port 52 may be vented, connected to an exhaust treatment system or connected to a condensing system. In FIG. 3, the cap 50 comprises a cap exhaust port 52 for venting pressure in the sparger tubular member 40 to the atmosphere. The cap 50 also comprises a gas chromatography port 54 that permits gas chromatography of a headspace. For example, the sparger tubular member 40 can include a micro-gas chromatographer (micro-gc). Further, the cap 50 comprises a sensor port 56 that includes a sensor lead 58 that extends from a sensor 60, such as a metal-oxide semiconductor (MOS) sensor and that can be connected with an analytic device 62.

Sparger tubular member 40 also includes an inlet 64 for feeding influent. The inlet 64 is disposed in the tubular members, positioned between the cap 50 and a connection between sparger tubular member 40 and bottom connector tubular member 42. The inlet 64 can provide a waste and by-product passage for a process being monitored or inlet 64 can be connected to a waste and by-product passage by a fluid connection for withdrawing a representative sample of waste or by-product. Influent to the sensing unit 38 establishes an aqueous level 66. A headspace 68 is defined above the aqueous level 66. Sparged materials, such as VOCs, can be monitored in the headspace 66.

Further, the sparger tubular member 40 comprises a gas inlet 72, which is positioned above the inlet 64 disposed between inlet 64 and cap 50. Gas inlet 72 permits inert gas, such as ambient air to enter the sparger tubular member 40. This arrangement equalizes pressures during flow without back pressure or vacuum. Inert gas inlet 72 can be disposed above the aqueous level 66. This positioning facilitates removal of VOCs from headspace 68. The sparger tubular member 40 also includes a sparger 74, which is disposed close to connection of sparger tubular member 40 to bottom connector tubular member 42. Sparger 74 permits inert non-reactive gas 78 to continuously flow through aqueous portion 70. The gas introduced via sparger 74 is inert to avoid reaction with VOCs or other materials in the aqueous portion 70. Exemplary gases that can be introduced via sparger 74 include air and nitrogen.

The tubular members of sensing unit 38 can comprise any appropriate material for fluid flow in which the materials will not be degraded, corroded, or otherwise adversely affected by influent, effluent or sparged contaminant. For example, the tubular members may comprise polyvinyl chloride (PVC) or thick-walled glass, polyacrylate, polycarbonate or another clear polymer resin that allows visual inspection.

The aqueous level 66 in the sensing unit 38 can be controlled by the P-trap tubular member 46 and venting and discharge tubular member 48. The venting and discharge tubular member 48 comprises a vent to the atmosphere, which is generally illustrated as 76, located at some point along the sensing unit 38 above aqueous flow path. Vent 76 provides atmospheric pressure and relief to the sensing unit 38.

Analytic devices, 62 and 63 that are connected to the sensing unit 38 can be selected from a variety of available process analyzers. For example, sensor 60 can be a MOS sensor and micro-gas chromatography sampler that is coupled between headspace 68 and analytic devices 62 and 63. The arrangement can provide near realtime monitoring and analyses. The term "real-time" means a processing system that controls an ongoing process and delivers its outputs or controls its inputs substantially immediately upon sensing. For example, a MOS sensor designated at 60 can deliver total hydrocarbon concentration data at response times of about 1 second. Further, a micro-gas chromatography system designated at 64 can provide VOC data at a response time of about 6 minutes.

The sensing unit 38 can further include a communication link such as a transceiver unit 26 to provide analyzed data to collector 22, which can include antenna 36 to receive data from any of sensing units 38 or from 18 and 20 as shown in FIGS. 1 and 2. Collector 22 receives contaminant information from sensing units 18 and 20 via lines 106. Collector 22 can be a data collection center that receives contaminant information from sensing units 18 and 20 or from other sensing units (not shown) that may be included in conjunction with carbon beds 14 and 16 or that can be located at other monitored sites.

Collector 22 can comprise an antenna 36 to receive data from the sensing units 18 and 20. The collector 22 can utilize the data as described or further transmit this data to controller 24 via communication line 108. The collector 22 and controller 24 can comprise various configurations. In one embodiment, collector 22 and controller 24 are contiguous units situated at a single location either in the vicinity of or remote from the monitored carbon beds 14 and 16. In another embodiment, collector 22 and controller 24 are removed from one another. In this embodiment, the collector 22 can be situated in the vicinity of the monitored beds 14 and 16 and the controller 24 can be remotely located.

The collector 22 can include a processor 80 that can analyze signals delivered via link 108 and that can generate information concerning influent or effluent characteristics. The data collection center processor 80 can include a "user friendly" data acquisition software package. The software package can transform information into easy to read real or virtual formats or into commands to directly control the operation of carbon beds 14 and 16. In one embodiment, the information can be collected and stored at the data collection center 22 to be accessed by a user or the information can be transmitted to controller 24 to be accessed by a user or to be processed to provide automatic control of influent line 102 via transmission line 110 connected to valve 82 or to provide automatic control of effluent line 104 via transmission line 112 connected to valve 84.

The controller 24, which can be a control center, can comprise any appropriate solid-state device, for example a computer designated 86. The control center 24 may include data acquisition capability, such as data acquisition software. Control center 24 can comprise a central processor for overall, system-level control, and separate sections to perform various different specific combination functions and other processes under control of the central processor section. The control center 24 can be implemented using a variety of separate dedicated, programmable integrated and other electronic circuits or devices. These devices include hardwired electronic, logic circuits including discrete element circuits and programmable logic devices. The programmable logic devices include a programmable logic device (PLD), programmable array logic (PAL), programmable logic array (PLA) and the like. The control center 24 can also be implemented using a suitably programmed general-purpose computer such as a microprocessor, microcontrol or other processor device such as a control processing unit (CPU) or microprocessing unit (MPU) in conjunction with one or more peripheral data and signal processing devices.

The controller 24 can produce hard copies of reports and provide computer readable electronic output, which can be accessed by a user or control device remote from the carbon adsorption zone 12 or even remote from control center 24. Control center 24 can be capable of processing information from a variety of adsorption sites or other treatment sites throughout the world. The control center 24 can be located with the data collection center 22 or can be located a remote long distance removed from the center 22 depending on the range of a communication link 108. The communication link 108 can be a phone modem, network connection, radio communication, cellular communication, satellite communication, web access communication or Internet access communication or combinations thereof. The particular construction of the communication link 108 depends on communication link types accessible at the data collection center 22, to the adsorption zone 12 or to the control center 24.

FIGS. 1 and 4 represent embodiments of the method and system of the invention. In FIG. 1, influent can be directed into either adsorption bed 14 or bed 16 depending on the activation of valve 82 by control center 24. Additionally, the method can be controlled so that influent is treated only in bed 14 or is treated in both beds 14 and 16 according to the activation of value 84 by control center 24. In FIG. 4, where like elements are identified by the same numerals as in FIG. 1, carbon adsorption beds 14 and 16 are connected in parallel with carbon adsorption bed 88. In this embodiment, influent flow can be alternatively directed into one of the three beds of the adsorption zone 12 according to the activation of three way valve 90. In this embodiment, the beds may have different adsorption characteristics. The appropriate bed for treating the influent is chosen from data accumulated at sensor 18 or by both sensors 18 and 20.

While preferred embodiments of the invention have been described, the present invention is capable of variation and modification and therefore should not be limited to the precise details of the examples. For example, the method and system embodied in FIG. 1 or in FIG. 4 can be used in conjunction with a vacuum extraction system. Vacuum extraction involves passing large volumes of air through or close to a contaminated spill or aquifer using an air circulation system. Organic compounds or fractions of mixtures of organic compounds volatilize or evaporate into the air and are transported to the surface.

In the vacuum extraction method, extraction wells and injection wells usually consisting of slotted, plastic pipes are placed in a contaminated soil. The injection wells force air into the ground to promote horizontal airflow in the direction of the extraction wells. Pumps or blowers reduce gas pressure in the extraction wells to further induce airflow between injection wells and extraction wells. The airflow passes through the contaminant source and scavenges contaminants in the form of VOCs for delivery to the extraction wells. The extraction wells then deliver a vapor phase contaminant to a treatment facility, such as a carbon bed treatment system.

In this embodiment, the method and system exemplified in FIG. 1 or FIG. 2, is a vapor-phase carbon adsorption method and system. Vapor-phase carbon adsorption is a remediation technology in which pollutants are removed from air by physical adsorption onto activated carbon grains. Carbon is "activated" for this purpose by processing the carbon to create porous particles with a large internal surface area (300 to 2,500 square meters or 3,200 to 27,000 square feet per gram of carbon) that attracts and adsorbs organic molecules as well as certain metal and inorganic molecules.

Commercial grades of activated carbon are available for specific use in vaporphase applications. The granular form of activated carbon is typically used in packed beds through which the contaminated air flows until the concentration of contaminants in the effluent from the carbon bed exceeds an acceptable level. Granular-activated carbon (GAG) systems typically consist of one or more vessels filled with carbon connected in series and/or parallel operating under atmospheric, negative, or positive pressure. The carbon can then be regenerated in place, regenerated at an off-site regeneration facility, or disposed of, depending upon economic considerations.

Carbon can be used in conjunction with steam reforming. Steam reforming is a technology designed to destroy halogenated solvents (such as carbon tetrachloride, $CCl_4$ and chloroform, $CHCl_3$, adsorbed on activated carbon by reaction with superheated steam (steam reforming) in a commercial reactor.

The invention includes changes and alterations that fall within the purview of the following claims.

What is claimed is:

1. A method of treating a contaminated fluid stream, comprising:
   providing a plurality of fluid-treatment zones that comprises at least a carbon adsorption zone to treat a contaminated fluid stream;
   sensing a characteristic of a flow of a contaminated fluid stream to a carbon adsorption zone;
   remotely monitoring said sensing;
   determining a treatment process scheme for treating said contaminated fluid stream, said determining comprising deciding a sequence of fluid-treatment zones through which said contaminated fluid stream flows;
   remotely providing signals as a result of said determining to fluid control devices associated with an operation of said fluid-treatment zones to actuate said fluid control devices to carry out said treatment process scheme;
   treating said contaminated fluid stream according to said treatment process scheme to remove at least a contaminant in said contaminated fluid stream to a level such that a treated fluid stream is dischargeable into an environment.

2. The method of claim 1, comprising treating said contaminated fluid stream in said at least a carbon adsorption zone according to said treatment process scheme that comprises employing said at least a carbon adsorption zone.

3. The method of claim 1, additionally comprising monitoring a treated aqueous effluent from said treating.

4. The method of claim 3, additionally comprising adjusting the treating of said contaminated fluid stream according to said monitoring of treated aqueous effluent.

5. The method of claim 1, wherein said treating comprises filtering said contaminated fluid stream in a filter zone and adsorbing contaminants in said carbon adsorption zone.

6. The method of claim 1, wherein said treating comprises stripping volatile contaminants from said contaminated fluid stream in a stripping zone and adsorbing contaminants in said carbon adsorption zone.

7. The method of claim 6, wherein said treating comprises filtering said contaminated fluid stream in a filter zone and adsorbing contaminants from filtered volatile contaminants in said carbon adsorption zone.

8. The method of claim 1, further comprising:
   sparging a non-reactive gas into said contaminated fluid stream to separate a volatile contaminant; and
   monitoring said volatile contaminant from said fluid stream.

9. The method of claim 1, further comprising:
   diffusing said contaminated fluid stream through a membrane to separate said contaminant from said fluid stream. and
   monitoring said separated contaminant.

10. The method of claim 1, wherein said fluid stream comprises groundwater and said method further comprises:
    intercepting said groundwater at an underground capture zone, pumping the groundwater from the capture zone to ground surface and treating said groundwater by removing contaminants in said carbon adsorption zone.

11. The method of claim 10, further comprising recharging said treated groundwater back into the underground, discharging said treated groundwater to a surface water body or discharging said treated groundwater to a municipal sewage plant collector.

12. The method of claim 1, wherein said monitoring comprises sampling said fluid stream.

13. The method of claim 1, wherein said monitoring comprises monitoring with a probe and a sensor.

14. The method of claim 1, wherein said monitoring comprises sensing a contaminant and transmitting a signal concerning said contaminant to a data collector.

15. The method of claim 14, wherin said data collector collects said signal and transmits information concerning said contaminant derived from said signal.

16. The method of claim 15, wherein said collector transmits said information to a remote monitor.

17. The method of claim 16, wherein said information is transmitted over a web connection, phone modem connection, radio connection, network connection, wireless connection, cellular connection, satellite connection, Internet connection or combinations thereof.

18. The method of claim 16, further comprising outputting a contaminant report from said remote monitor.

19. The method of claim 1, comprising forming said contaminated fluid stream by vacuum extraction from a contaminated ground source.

20. The method of claim 1, comprising treating said contaminated fluid stream by a vapor-phase carbon adsorption method.

21. The method of claim 1, comprising treating said contaminated fluid stream by a vapor-phase carbon adsorption method in combination with steam reforming.

22. A method of treating a contaminated fluid stream, comprising:
    sensing a characteristic of a flow of a contaminated fluid stream to a carbon adsorption zone;
    remotely monitoring said sensing to determine a treatment for said contaminated fluid stream;

treating said contaminated fluid stream according to said monitoring;

wherein said monitoring comprises sampling said contaminated fluid stream, and said sampling comprises sparging a volatile organic compound from said contaminated fluid stream and sensing said volatile organic compound.

23. A method of treating a contaminated fluid stream, comprising:

sensing a characteristic of a flow of a contaminated fluid stream to a carbon adsorption zone;

remotely monitoring said sensing to determine a treatment for said contaminated fluid stream;

treating said contaminated fluid stream according to said monitoring;

wherein said monitoring comprises sampling said contaminated fluid stream; and said sampling comprises:

providing a network of tubular members that are interconnected to each other to define a fluid passage and a sparger disposed within said passage;

flowing fluid stream within the vicinity of said sparger;

causing a gas from said sparger to flow through said fluid stream to sparge a volatile organic compound and to convey said volatile organic compound to a forming headspace;

sensing said volatile organic compound within said headspace to determine a volatile organic compound content of said contaminated fluid stream.

24. A fluid-treatment system, comprising:

a plurality of fluid-treatment zones that comprise at least a carbon adsorption zone to treat a contaminated fluid stream;

at least a first sensor that senses a characteristic of a flow of said contaminated fluid stream prior to a treatment of said contaminated fluid stream;

a monitor to receive information concerning said characteristic from said sensor to determine a treatment process scheme for treating said contaminated fluid stream and to actuate fluid control devices associated with an operation of said fluid-treatment zones to treat said contaminated fluid stream by removing at least a contaminant from said contaminated fluid stream to a level such that a treated fluid stream is dischargeable into an environment;

wherein said monitor is situated at a location remote from said fluid-treatment zones, said treatment scheme comprises deciding a sequence of fluid-treatment zones through which said contaminated fluid stream flows, and said fluid control devices receive signals for their actuation from said monitor as a result of said deciding.

25. The system of claim 24, further comprising a second sensor to monitor a treated aqueous effluent from said carbon adsorption zone.

26. The system of claim 25, wherein said monitor receives information from said second sensor, said information being used to effect a control of said carbon adsorption zone to treat said contaminated aqueous composition.

27. The system of claim 24, wherein said carbon adsorption zone further comprises a filter zone to filter said contaminated fluid stream.

28. The system of claim 24, wherein said carbon adsorption zone further comprises a stripping zone to strip volatile contaminant from said contaminated fluid stream.

29. The system of claim 24, further comprising a sparger to sparge a nonreactive gas into said contaminated fluid stream.

30. The system of claim 29, further comprising a diffuser to diffuse said contaminated fluid stream through a membrane to separate a volatile contaminant wherein said volatile contaminant is sensed by said sensor.

31. The system of claim 24, further comprising a transmitter associated with said sensor to transmit a signal concerning said contaminant.

32. The system of claim 24, further comprising a transmitter associated with said first sensor to transmit a signal concerning contaminants contained in said contaminated fluid stream.

33. The system of claim 32, wherein said collector is capable of transmitting a signal concerning said contaminant t o said monitor.

34. The system of claim 33, further comprising a communication link that interconnects the data collector and the monitor, the communication link capable of transmitting said signal to enable a user at the monitor to obtain information concerning the contaminant.

35. The system of claim 34, wherein the communication link comprises a web connection.

36. The system of claim 34, wherein the communication link comprises a network.

37. The system of claim 34, wherein the communication link comprises a phone modem connection, radio communication connection, network communication connection, wireless communication system connection, cellular communication connection, satellite communication connection, web connection, Internet connection or combinations thereof.

38. The system of claim 34, further comprising a two-way communication between said collector and said sensor to permit selection, activation, de-activation, modification, fine-tuning, manipulation or resetting of said probe.

39. The system of claim 34, further comprising a two-way communication between said collector and said first sensor to permit selection, activation, de-activation, modification, fine-tuning, manipulation or resetting of a probe of said first sensor.

40. The system of claim 32, wherein the collector comprises a controller.

41. The system of claim 40, wherein the controller comprises a computer.

42. The system of claim 32, wherein the collector comprises a transceiver.

43. The system of claim 42, wherein the transceiver comprises an integrated antenna or a separate antenna.

44. The system of claim 24, wherein the first sensor comprises an in-situ sensor, vapor sensor, chemical sensor, fiber optics sensor, acoustic wave sensor solidstate sensor, metal oxide sensor, an electrochemical sensor or combinations thereof.

45. The system of claim 24, wherein said at least a first sensor comprises a plurality of different sensors to sense different contaminants.

* * * * *